United States Patent [19]
Mitchell et al.

[11] Patent Number: 5,147,325
[45] Date of Patent: Sep. 15, 1992

[54] RIGID NEEDLE SHIELD

[75] Inventors: Jay F. Mitchell, Deland; Roger L. Crouse, Ormond Beach; Herbert W. Lesher, Lake Helen, all of Fla.

[73] Assignee: Sherwood Medical Company, St. Louis, Mo.

[21] Appl. No.: 695,365

[22] Filed: May 3, 1991

[51] Int. Cl.⁵ .................................. A61M 5/32
[52] U.S. Cl. .......................... 604/192; 604/263
[58] Field of Search .............. 604/187, 192, 198, 263; 206/365, 366, 367

[56] References Cited

U.S. PATENT DOCUMENTS

| | | |
|---|---|---|
| 2,671,450 | 3/1954 | Dann . |
| 2,688,963 | 9/1954 | Smith . |
| 2,831,483 | 4/1958 | Delorenzo . |
| 2,847,996 | 8/1958 | Cohen et al. . |
| 3,865,236 | 2/1975 | Rycroft ............................ 206/364 |
| 4,237,882 | 12/1980 | Wickham . |
| 4,317,446 | 3/1982 | Ambrosio et al. . |
| 4,334,536 | 6/1982 | Pfleger . |
| 4,365,626 | 12/1982 | House . |
| 4,430,082 | 2/1984 | Schwabacher ...................... 604/263 |
| 4,485,918 | 12/1984 | Mayer .............................. 206/366 |
| 4,635,201 | 1/1987 | Ambrose et al. ..................... 604/192 |
| 4,735,617 | 4/1988 | Nelson et al. ...................... 604/192 |
| 4,742,910 | 5/1988 | Staebler ............................ 206/365 |
| 4,752,290 | 6/1988 | Schramm ........................... 604/198 |
| 4,826,488 | 5/1989 | Nelson et al. ...................... 604/192 |
| 4,850,970 | 7/1989 | Sutherland ......................... 604/117 |
| 4,872,552 | 10/1989 | Unger .............................. 206/365 |
| 4,897,083 | 1/1990 | Martell ............................. 604/192 |
| 4,900,309 | 2/1990 | Netherton et al. ................... 604/192 |
| 4,915,697 | 4/1990 | Dupont ............................. 604/192 |
| 4,931,048 | 6/1990 | Lopez .............................. 604/110 |
| 4,964,866 | 10/1990 | Szwarc ............................. 604/192 |

Primary Examiner—John D. Yasko
Attorney, Agent, or Firm—Andrew J. Beck; Montgomery W. Smith; Gene B. Kartchner

[57] ABSTRACT

The present invention relates to a shield for use on a prefilled hypodermic syringe assembly. The shield is intended to be retrofitable over a sheath/needle sub-assembly of the hypodermic syringe assembly in such a manner that insertion of the sheath/needle sub-assembly into the shield can be simply and easily accomplished by a medical worker, and subsequent extraction of the sheath from the shield is prevented by retention members which are formed from the housing of the shield, and which protrude into the chamber to hold the sheath. The retention member are formed so as to allow the sheath to be slidable into the chamber of the shield, yet engage the exterior surface of the sheath to resist extraction thereof once the sheath has engaged the retention members.

45 Claims, 3 Drawing Sheets

RIGID NEEDLE SHIELD

BACKGROUND OF THE INVENTION

1. Field of the Invention

The present invention relates to a shield for a hypodermic syringe assembly. More particularly, the present invention relates to a shield which can be retrofitted over an existing sheath/needle cannula sub-assembly of a hypodermic syringe assembly. Even more particularly, the present invention relates to a rigid shield which can be retrofitted over a resilient sheath which is being used to seal the distal end of a needle cannula of a prefilled hypodermic syringe prior to its use, the shield functioning to prevent needle sticks due to accidental piercing of the resilient sheath by the needle cannula.

2. Description of the Prior Art

It is common practice in the preparation of medications for use by medical workers, to pre-packaging the medications directly within a sealed hypodermic syringe assembly when such is a necessary vehicle for administration of the medication to a patient. According to this practice, a hypodermic syringe is sterilized and then prefilled with a predetermined amount of medication in a sterile environment, and the medication is sealed into the syringe by sealing the distal end of the needle cannula. The syringe is then packaged singly or in a predetermined quantity, into packaging which can be sterilized to maintain the sterility of the syringes until the medication is to be administered to a patient. In following this procedure, it has often been the practice to seal the distal end of the needle cannula with a resilient needle sheath. A sheath of this type is usually formed of a resilient rubber material with an elongate cavity therein which can accept the needle cannula. Generally, the sheath is formed so as to be capable of forming a friction fit with the hub of the needle cannula to hold the sheath in position over the needle. The cavity is sized so as to either fit snugly around the distal tip of the needle cannula, or to allow the distal tip of the needle cannula to pierce the distal end of the sheath and become embedded therein. In either case, the sheath effectively seals the tip of the needle cannula to prevent fluid from flowing therethrough out of the syringe during storage or prior to use.

Although the resilient needle sheath is generally quite successful in sealing the needle cannula, there remains serious concerns in the use thereof. Specifically, due to the piercability of the sheath, there exists a possibility of medical workers accidentally receiving a needle stick while using the syringe. This usually occurs either during preparation of the syringe for administration of medication to a patient, or during disposal procedures therefor. For example, since the sheath is formed of a resilient rubber, a minimal force improperly applied is all that is needed to cause the needle tip to penetrate (and even pierce entirely through) the sheath. Therefore, inadvertent pressure on the tip of the sheath during handling of the syringe assembly, may cause the needle to pierce entirely through the sheath's distal end and become exposed.

Further, medical workers often attempt to reinsert the needle into the sheath after the syringe has been used and prior to its disposal, even though this procedure is generally not recommended. Misalignment of the needle with the sheath during reinsertion can cause the tip of the needle to pierce through the side of the sheath where it may contact the hand of the medical worker holding it. Needle protrusion of this nature can readily occur since the tip of commonly used needles is ground off-center (i.e. on a bias) and therefore proceeds in a non-linear path when piercing the resilient sheath material. The needle tends to follow the off centered point as it passes through the sheath and in effect "skives off" in an arcing path of travel as it passes through the sheath material. If a medical worker is not extremely careful to let the needle center itself in the sheath cavity during reinsertion, the needle may inadvertently contact the side of the sheath cavity and pierce through the sheath material in a surprisingly unexpected direction, catching the medical worker off guard and likely causing a stick to the hand of the medical worker holding the sheath.

Although rigid, substantially impenetrable shields are commonly used to cover needle cannulas of hypodermic syringe assemblies, they are generally unsuitable for use on syringes which have been prefilled with a fluid such as a liquid medicament, due to their inability to seal the end of the needle cannula from fluid flow therethrough during storage and prior to use.

There have been attempts in the past to develop a substantially impenetrable shield which can be positioned over a resilient sheath commonly used on prefilled syringes in order to provide added protection to a medical worker from accidental needle sticks. For example, U.S. Pat. No. 4,964,866 to Szwarc discloses a needle shield assembly for use on a prefilled syringe. The assembly includes a resilient sheath, generally of the above described prior art construction, permanently enclosed in a rigid shield. The entire needle shield assembly (including the resilient sheath permanently enclosed in the rigid shield) is positioned over the needle cannula and thus seals the lumen of the needle cannula while simultaneously aiding in the prevention of needle sticks due to an accidental protrusion of the needle through the sheath.

Although this invention is a substantial improvement over the use of a resilient sheath alone in preventing accidental needle sticks, it is nevertheless somewhat limited in its use, and generally unadaptable to the myriad of different structural designs of commonly used prefilled hypodermic syringe assemblies. Specifically, the Szwarc needle shield assembly cannot be conveniently used to "retrofit" previously filled, sheathed, and sterilized prefilled hypodermic syringe assemblies.

Also, the design of the Szwarc device prevents its use as a retrofittable sub-assembly over a previously sheathed hypodermic syringe. This is because the Szwarc shield is manufactured in such a way as to require its assembly about the sheath prior to the sheath's placement over the needle cannula. This prevents any use of Szwarc over a previously sheathed and sterilized needle cannula. Prematurely removing the sterilized sheath of a needle/sheath assembly would be required in order to replace it with the encapsulated sheath of the Szwarc shield/shield.

An attempt to use the Szwarc device in such a retrofit manner would necessitate the removal of the original resilient sheath which was placed over the needle cannula prior to its sterilization, and subsequent insertion thereover of Szwarc's sheath/needle sub-assembly. Such a procedure would likely not be recommended due to the possibility of contamination of the needle cannula during the retrofitting process.

Also since it is important for a sheath to be properly sized in order to seal a needle cannula, the Szwarc device, in order to properly function to seal a needle cannula, must generally be manufactured to dimensions required by a particular syringe assembly design. Therefore, other needle cannula's (and sheath's therefor) of a substantially different size (e.g. shorter or longer in length) than specifically anticipated by Scwarc's design, cannot be used therewith.

There exists therefore a need to develop a shield which can be retrofitted over a sheath of a prefilled hypodermic syringe assembly by a medical worker, after the sheath has been positioned and sterilized, and prior to using the assembly. Further, it is necessary that such retrofitting procedure not compromise the sterility of the needle prior to its use nor require a premature removal of the sheath in order to install the shield.

There also exists a need in the prior art to develop a needle shield which can be used on various sizes and lengths of needle cannula and sheaths therefor.

Staebler, in U.S. Pat. No. 4,742,910, teaches another needle sheath holder which consists of a hollow barrel member adapted to be held in the hand of a medical worker. Staebler also includes a protective plate mounted to an open end of the barrel through which a sheath/needle sub-assembly of a hypodermic syringe assembly can be inserted. The plate is designed to protect the medical worker's hand during the insertion process. Finally, the Staebler device further includes a plurality of flexible gripper members attached at the barrel opening which are intended to engage the needle sheath so as to retain the needle sheath within the barrel.

Although the Staebler device seems an improvement over the Szwarc device in its retrofit capabilities, it nevertheless suffers from several drawbacks. Most notably, the Staebler device includes three separate parts (i.e., the barrel, the plate, and the gripper members) which must be individually manufactured and subsequently assembled, resulting in relatively expensive manufacturing costs. Further, it is not readily evident from the Staebler disclosure that a sheath formed of resilient material, such as resilient rubber (as opposed to what seems to be shown by Staebler as a relatively rigid sheath) could be successfully inserted into and retained by Staebler's barrel shield.

There therefore exists a need in the prior to develop a retrofittable shield for use over a resilient sheath of a hypodermic syringe assembly which is simple in design and inexpensive to manufacture.

In U.S Pat. No. 4,636,201, Ambrose et al. teaches the placement of a rigid shield over a rubber sheath of a hypodermic syringe. The rigid shield includes a plurality of spaced teeth members which are located at (and essentially form) the opening of the shield through which the sheath/needle sub-assembly of the syringe assembly is to be inserted. At least a pair of the teeth of the shield include a lip which projects inwardly toward the center of the opening to close in over the proximal end of the sheath once completely inserted into the shield.

Although Ambrose et al. allows a retrofit procedure to be performed on a hypodermic syringe assembly in a manner similar to Staebler, and also anticipates use of its device over a resilient sheath, there are nevertheless several important drawbacks of the Ambrose et al. device. Specifically, due to the location of the teeth on the Ambrose et al. device, it is difficult to ensure that a proper grip of the teeth about the proximal end of the sheath will occur. Many prior art sheath designs call for insertion of the sheath over the syringe needle hub until the proximal end of the sheath abuts a shoulder of the hub (generally at a location where the hub changes from a larger to a smaller diameter). This is a common design characteristic of a syringe hub and is useful to insure sealing of the sheath thereover. It also gives medical workers a visual and tactile indication that the sheath is properly positioned on the hub.

In such designs, there is no room for the teeth of the Ambrose et al. device to slip between the hub shoulder and the proximal end of a properly placed sheath in order to grip and retain the sheath in the manner Ambrose discloses. Due to this fact, use of the Ambrose et al. device on many common needle hub and sheath designs will not allow the teeth of the shield to properly attach themselves about the proximal end of the sheath. Only a syringe having a sheath/needle design which does not include abutment of the proximal end of the sheath against a shoulder of the needle hub will function properly with the Ambrose et al. device. Such a design limitation substantially inhibits the use of the Ambrose et al. device for purposes of retrofitting various common prefilled hypodermic syringe assemblies.

Further, medical workers may be hesitant to employ the Ambrose et al. device for retrofitting over sheaths of hypodermic syringe assemblies if they feel the shield may be less than completely reliable in gripping and retaining the sheath (e.g., due to the difficulties it may encounter if used on syringe assemblies having a hub design which differs from that shown in the Ambrose et al. disclosure).

Although it may seem at first glance that this problem may be avoided by initially partially removing the sheath from the needle hub prior to inserting the sheath into the Ambrose et al. shield (in order to space the proximal end of the sheath from the hub shoulder) such a procedure would likely be very unpopular with medical workers due to the inconvenience thereof. Such would also likely fail to resolve the problem since during insertion, the teeth of the Ambrose et al. needle shield contact and are forced apart by the sheath as the shield is positioned thereover. The teeth therefore force the sheath in the direction of the needle hub during placement of the shield. Subsequently, any attempt to separate the proximal end of the sheath from a shoulder of the needle hub prior to insertion of the sheath would be opposed by the force of the shield teeth on the sheath. The insertion force would likely reposition the proximal end of the sheath into abutting relationship with the shoulder of the needle hub prior to complete insertion of the sheath into the shield. The result would again be that the teeth would not be able to properly and securely grip the proximal end surface of the sheath.

There therefore exists a need in the prior art to develop a shield which can be retrofitted over an existing sheath of a prefilled hypodermic needle assembly and retain the sheath in the shield during subsequent removal and/or insertion of the needle into the sheath, without regard to the particular design of the sheath/needle hub connection.

Although the above prior art discloses a plurality of rigid shields used to protect medical workers against needle sticks from hypodermic syringes having resilient sheaths, there nevertheless continues to be a need for a rigid, substantially impermeable needle shield which can be simply and easily retrofitted over a range of sizes and designs of prefilled hypodermic syringes, without compromising the sterility of the needle cannula and with substantial reliability of retention of the sheath in the shield. Further, such a needle shield is needed which can also be manufactured as a single integral unit requiring no assembly of individual parts, so as to be simple to manufacture and relatively inexpensive.

OBJECTS AND SUMMARY OF THE INVENTION

It is an object of the present invention to provide a shield for use on a prefilled hypodermic syringe having a resilient sheath thereover, which is easily retrofittable over the sheath and which retains the sheath therein once the shield is retrofitted thereover.

It is another object of the present invention to provide a retrofittable shield, such as described above, which can be used on a variety of sizes of sheath/needle cannula sub-assemblies of prefilled hypodermic syringe assemblies.

It is further an object of the present invention to provide a shield as described above which is easily manufacturable as a single integral unit in an efficient and inexpensive manner.

These and other objects of the present invention are disclosed, by way of example and not necessarily by way of limitation, in presently preferred embodiments thereof. A needle shield made in accordance with the principles of the present invention includes an elongate tubular housing having formed therein an elongate chamber, preferably open at its proximal end. The housing includes retention members preferably formed therefrom, which protrude into the chamber and which may be oriented in a predetermined pattern and shaped so as to allow insertion of a resilient sheath (which covers a needle cannula) into the chamber with minimal resistance, yet allow sufficient gripping to inhibit removal of the sheath from the chamber after insertion. The present invention is intended to function to cause the sheath to remain inside the shield once inserted therein, throughout all subsequent normal uses of the hypodermic syringe assembly.

If desired, the retention members may be oriented in a plurality of specific longitudinal and/or circumferential positions within the chamber of the shield, to allow the shield to be used in conjunction with a plurality of different sizes of sheath/needle cannula sub-assemblies of hypodermic syringe assemblies.

For example, the retention members may take the form of longitudinally and circumferentially oriented ribs positioned in uniformly spaced apart relationship around the circumference and along the longitudinal dimension, respectively, of the chamber. Alternatively, more than one set of ribs either longitudinally or circumferentially oriented, may be positioned in the chamber, with each set being rotated if desired, so as to align each rib of one set between the ribs of another. Each retention member, or set of retention members, may be located in the chamber of the shield so as to allow a particular shield to be usable on a variety of sheath/needle cannula lengths.

Further, if desired, a pair of longitudinal slots may be formed at circumferentially opposed location in the proximal portion of the shield. The slots allow the shield to be squeezed at the proximal end thereof in order to increase the gripping force of the shield on the resilient sheath. Also if desired, one or more circumferentially oriented retention members, such as ribs, may be formed within the chamber at the proximal end thereof, so as to be forced into the sheath as a result of the squeezing, in order to increase the gripping power against the sheath.

In one preferred method of manufacture of a needle shield in accordance with the principles of the present invention, the housing of the shield may be formed along with the elongate channel and the retention members therein in a single operation step, such as by injection molding or the like.

In a preferred method of use of the present invention, a syringe assembly, such as a prepackaged, sterile, prefilled syringe assembly which includes a sheath/needle cannula sub-assembly, can be removed from its sterile packaging (if necessary) by a medical worker, and a shield formed in accordance with the principles of the present invention, taken from its own prepackaged sterile container (if necessary), can be slid over the sheath/needle sub-assembly. Due to the various possible locations of retention members within the chamber of the shield, the sheath/needle cannula sub-assembly need be of no specific length to be properly accommodated within the chamber of the shield and adequately retained therein against extraction. When it is desired to use the hypodermic syringe assembly, the medical worker need merely remove the shield from the syringe assembly, which simultaneously, due to the interengagement of the retention members of the shield with the sheath, removes the sheath from the needle cannula.

Also, if desired or necessary, if the slots are provided in the shield, the medical worker may squeeze the shield prior to and during removal of the shield and sheath from the syringe, in order to insure proper separation of the sheath from the needle hub when the shield is removed. This may become necessary for syringe assemblies in which the hub and the sheath have become stuck together due to natural adhesion characteristics of the hub and sheath materials.

After use of the syringe assembly, the shield, along with the sheath therein, can be repositioned over the needle cannula if desired, without the fear of needle sticks occurring due to accidental piercing of the sheath by the needle cannula during reinsertion thereof.

The needle shield of the present invention may optionally be formed with the chamber having an open or closed distal end, and/or may optionally include stopper elements in the chamber at the distal end thereof for preventing over insertion of the sheath.

These and other objects and advantages of the present invention will become apparent from the following more detailed description when taken in conjunction with the accompanying drawings in which like elements are identified with like numerals throughout.

DETAILED DESCRIPTION OF THE PREFERRED EMBODIMENTS

In the exemplary drawings, used for the purposes of illustration, an embodiment of a needle shield made in accordance with the principles of the present invention is referred to generally by the reference numeral 10. The shield 10 is provided for use with the prefilled hypodermic syringe assembly 11 in order to prevent needle sticks to a medical worker from needle cannula 12.

Figure 1:
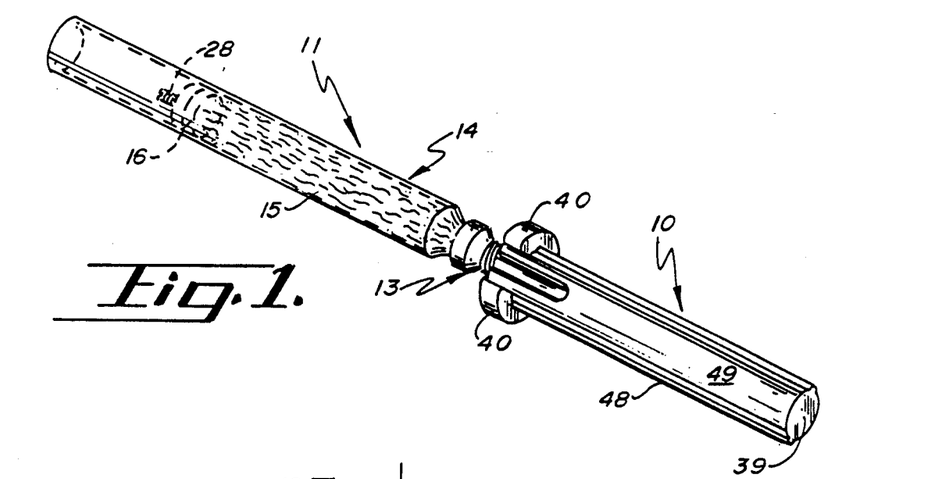
FIG. 1 is a perspective view of a preferred embodiment of a needle shield formed in accordance with the principles of the present invention, affixed to a prefilled hypodermic syringe assembly.
Figure 2:
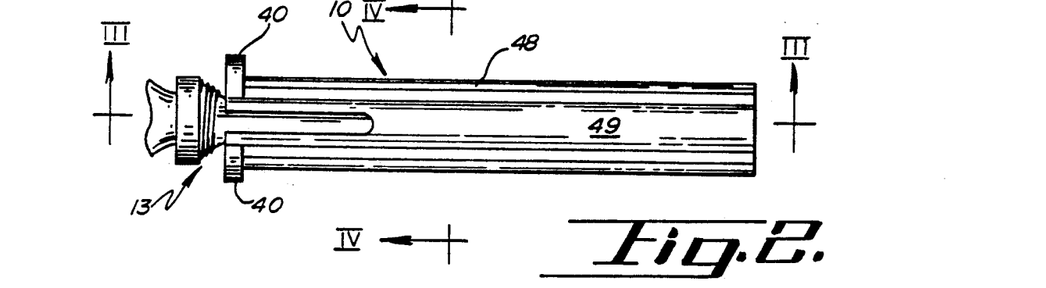
FIG. 2 is a side elevation view of the needle shield of FIG. 1 made in accordance with the principles of the present invention, affixed over the sheath/needle cannula sub-assembly portion of the prefilled hypodermic syringe assembly.
Figure 3:
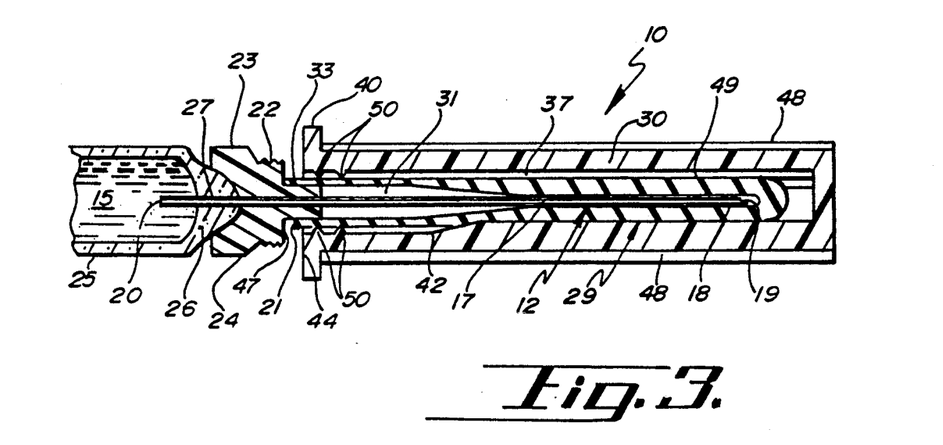
FIG. 3 is a longitudinal cross-sectional view of the needle shield and sheath/needle cannula sub-assembly of FIG. 2 taken along line III—III of FIG. 2.

As best shown in FIGS. 1-3, the prefilled hypodermic syringe assembly 11 generally includes a needle cannula 12 affixed by hub 13 to a syringe barrel 14. The barrel 14, commonly made of transparent glass, contains a fluid medicament 15 which is retained therein by piston 16.

The needle cannula 12 is formed with a lumen 17 extending through the entire length thereof, and includes a distal opening 18 adjacent its beveled distal tip 19. A proximal opening 20 of the needle cannula 12 is in fluid communication with the lumen 17 and the interior of the barrel 14.

The needle cannula 12 is affixed to the barrel 14 by hub 13. The hub 13 forms a distal cylindrical surface 21, an intermediate cylindrical surface 22, and a proximal cylindrical surface 23, each of which function to allow a friction fit of the hub 13 with other elements of the syringe assembly 11 in a manner as will be further explained below. The hub 13 also includes a cavity 24 through which the needle cannula 12 passes, and an abutment shoulder 47.

The barrel 14 of the syringe assembly 11 is preferably formed of a transparent glass sidewall 25 of cylindrical shape, which includes a closed tip 26 at the distal end thereof. The tip 26 is affixed in fluid tight permanent connection to cavity 24 of the hub 13, and also includes a channel 27 into which the needle cannula 12 is permanently affixed in a well known fluid-tight manner.

During use of the hypodermic assembly 11, the fluid medicament 15 is forced through opening 20 of the lumen 17 of the needle cannula 12, by forcing piston 16 in a distal direction in barrel 14. However, prior to movement of piston 16, it is intended that a piston arm (not shown) be attached to threaded extension 28 for convenience of operation.

Figure 4:
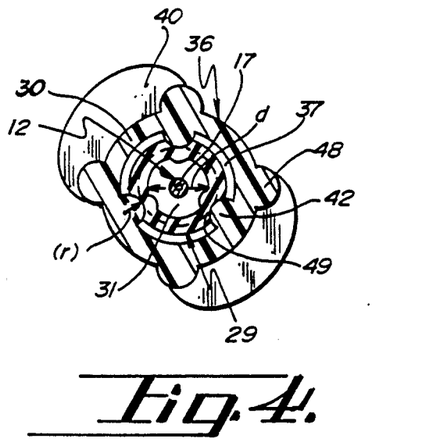
FIG. 4 is a perpendicular cross-sectional view of the needle shield and sheath/needle cannula sub-assembly of FIG. 2 taken along line IV—IV of FIG. 2.
Figure 5:
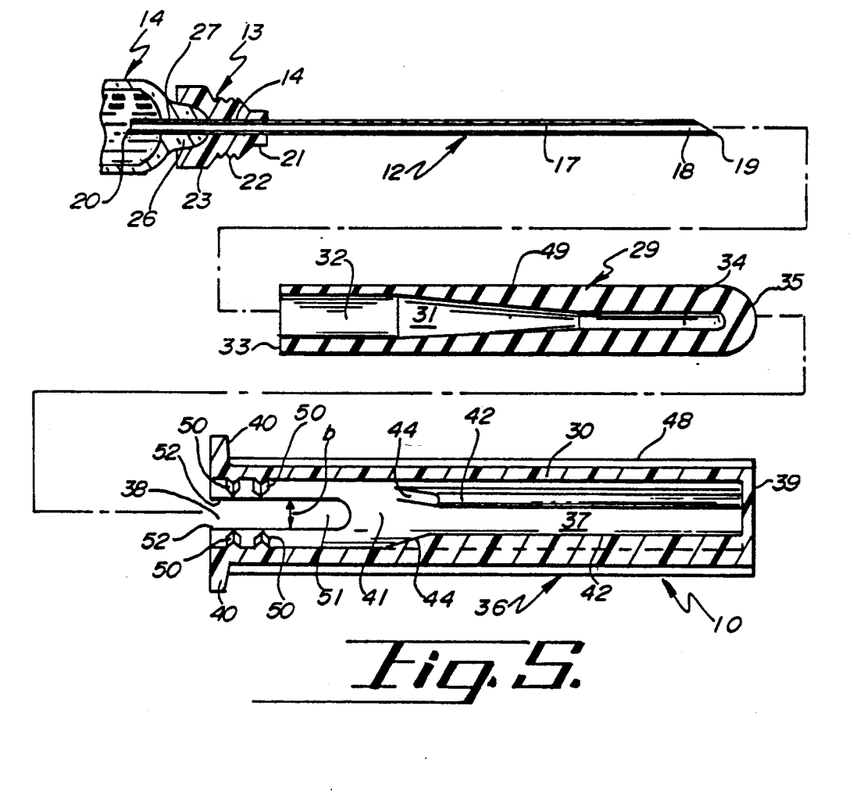
FIG. 5 is an expanded cross-sectional view of a preferred embodiment of the needle shield of the invention, and the sheath/needle cannula sub-assembly of FIG. 3.

As best shown in FIGS. 3-5, the sheath 29 is formed of an elongate cylindrical plug 30 of resilient material, such as rubber, and includes a cavity 31 sized to accept the needle cannula 12, with the proximal portion 32 thereof sized to allow its retention over the cylindrical surface 21 of hub 13 in a friction fit connection. The annularly shaped proximal end surface 33 of the sheath 29 is intended to be located in abutting relationship with the shoulder 47 of hub 13 when the sheath 29 is properly positioned over the needle cannula 12.

Cavity 31 also includes a distal portion 34, formed of a reduced diameter which is equal to, or only slightly greater than, the outer diameter of the needle cannula 12. When the needle cannula 12 is properly inserted in the sheath 29, the distal end 35 of the sheath 29 (which forms distal portion 34 of the cavity 31), effectively seals the distal opening 18 of the lumen 17 and substantially retains the fluid medicament 15 within the confined area of the barrel 14 and the lumen 17.

An alternative embodiment (not shown) of the sheath 29 may include forming the cavity 31 such that no distal portion 34 thereof exists. Therefore, instead of cavity 31 extending from proximal opening 32 in a distal direction in a gradually reducing diameter through distal portion 34 at the distal end 35 thereof, the cavity 31 stops well short of the distal end 35 leaving the remainder of the distal end 35 of the sheath 29 uniformly formed of resilient material. A needle cannula 12 inserted into this alternative type sheath 29 pass through the cavity 31 and pierces into the distal end 35 of sheath 29 until the lumen opening 18 is completely embedded in the resilient material forming distal end 35 (and until the opening 32 and proximal end surface 33 of the sheath 29 become properly positioned on the hub 13 in the manner as explained above). Since the lumen opening 18 of the needle cannula 12 is completely embedded within the resilient material forming the sheath 29 when in this position, the fluid medicament 15 is therefore completely sealed within barrel 14 and lumen 17.

As far as the needle shield 10 of the present invention is concerned, either design of sheath 29, including sheaths having other types of inner cavities 31 designed for sealing the distal opening 18 of a needle cannula 12, are hereby noted as being compatible for use therewith. The needle sheath 29 as shown herein is intended only to be exemplary of the types of needle sheaths which can be accommodated by the needle shield 10 of the present invention.

As will be referred to throughout this disclosure, the term "hypodermic syringe assembly 11" is intended to be understood as describing the needle cannula 12, hub 13, barrel 14 and sheath 29. Further as will be referred to herein, the term "sheath/needle cannula sub-assembly" is intended to identify the portion of the hypodermic syringe assembly 11 which includes sheath 29 and needle cannula 12.

As best shown in FIGS. 3-6, the needle shield 10 of the present invention may include a generally elongate cylindrically-shaped housing 36 formed of a relatively rigid material so as to be generally impermeable to penetration by the needle cannula 12. Any common well-known metal or polymeric material exhibiting these characteristics may be used, the preferred embodiment of the present invention being formed of either polypropylene, polyethylene, or a mixture thereof.

The housing 36 of the shield 10 has formed therein an elongate generally cylindrical chamber 37. The chamber 37 is formed with at least a proximal end opening 38 through which the sheath/needle cannula sub-assembly can be inserted.

If desired, although not required by the present invention, a distal end closure 39 may be formed to close the distal end of the chamber 37. If present, the distal end closure 39 can function to prevent over insertion of a sheath 29 within chamber 37, by functioning as a stop against which distal end 35 of the sheath 29 must ultimately abut when completely inserted into chamber 37. Alternatively, the distal end of chamber 37 may be left open, i.e., formed without distal end closure 39 (see FIG. 9), and stopping members 46 may be formed therein to function as stops for preventing the distal end 35 of sheath 29 from passing therebeyond during insertion. It should be well noted that stopping members 46 and/or distal end closure 39, are both optional structural features of the shield 10 of the present invention and may be used together, singly, or neither at all, as desired.

Figures 6, 8, 9:
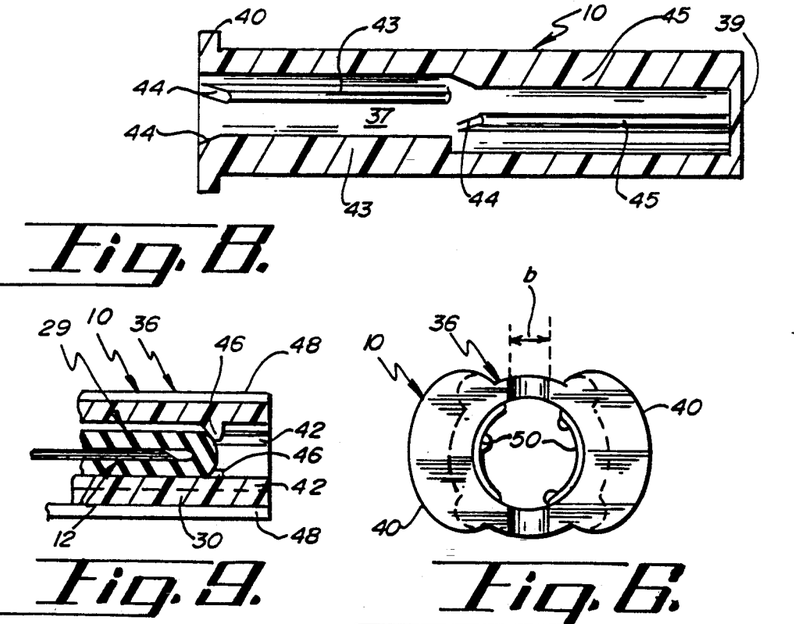
FIG. 6 is an end view of the shield of FIGS. 1-5, without the sheath/needle cannula sub-assembly.
FIG. 8 is a longitudinal cross-sectional view of a third preferred embodiment of a needle shield formed in accordance with principles of the present invention.
FIG. 9 is a cross-sectional view of the distal end of a shield formed in accordance with the principles of the present invention, showing a alternative distal end design of the shield.

As best shown in FIG. 6, the open proximal end 38 of chamber 37 may include a pair of semi-circular projections 40 extending around a major portion of the circumference thereof to protect the medical worker's hand during operation of the shield 10. The projections 40 may be of any radial dimension desired depending on the particular intended use of the shield 10 and the degree of user safety required. For example, should it be a routine necessity after a particular use of the present invention that the shield 10 be re-inserted over a used needle cannula 12, the projections 40 may be formed of a generally large radial diameter in order to increase protection to the worker's hand in case of inadvertent misalignment of the needle cannula 12 with the proximal end opening 38 of the shield 10 during reinsertion. If however, the shield 10 is intended to be used only for protection during storage and prior to use of the syringe assembly 11, the flange 40 may be of a smaller radial diameter (as shown in the drawings), or may be omitted entirely from the shield 10, as desired.

As best shown in FIG. 3, the interior surface 41 of chamber 37 is generally cylindrical in shape, and sized to a diameter which is intended to be slightly larger than the diameter of the exterior surface 49 of the sheath 29. At at least one location on interior surface 41, a retention member 42 protrudes therefrom into the chamber 37 which is located so as to contact the exterior surface 49 of the sheath 29 when the sheath is inserted into the chamber 37. The retention member 42 is designed to allow the sheath surface 49 to slide therealong as long as the sheath 29 is moving in the direction of its insertion into chamber 37, with the abutment of the proximal end 33 of the sheath against the shoulder 47 of the hub 13 counteracting the frictional force between the retention member 42 and the sheath surface 49.

Once sheath 29 has been inserted a substantial distance into chamber 37, attempted extraction of the sheath 29 causes the retention member 42 to force against surface 49 in an amount proportional to the force being used in extracting the sheath 29 from the chamber 37. In other words, force used to attempt an extraction of the sheath 29 from chamber 37 is opposed by the retention member 42. Thus, attempted removal of the shield 10 from the sheath 29 results instead, in the removal of sheath 29 from the needle cannula 12.

Figure 7:
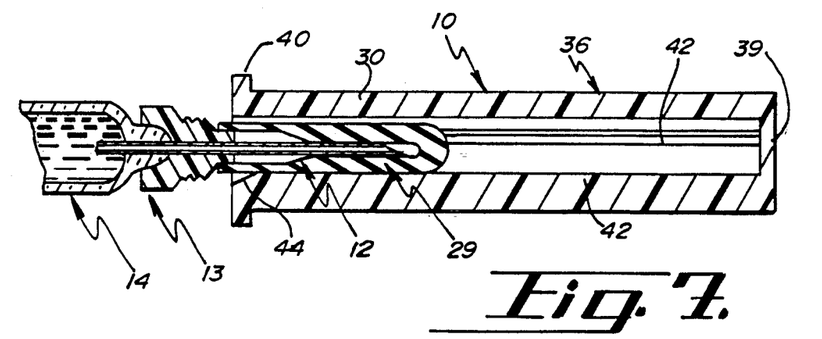
FIG. 7 is a cross-sectional view of a second preferred embodiment of the needle shield formed in accordance with the principles of the present invention, being used with an alternative type sheath/needle cannula sub-assembly.

In the particular embodiment of the shield 10 as shown in FIGS. 1–6 and in the second preferred embodiment as shown in FIG. 7, the retention member 42 is formed directly from the sidewall 36 of the shield 10 integrally with the sidewall in a single injection molding procedure. Each retention member is oriented generally longitudinally along a major portion of the length of chamber 37 and extends inwardly into chamber 37 a uniform distance from the chamber sidewall 41 along the entire length thereof. The retention member 42 therefore takes the form of a rib which is generally semi-circular in cross-section and which presents a semi-cylindrical surface toward to the interior of the chamber 39.

The retention member 42 may be used alone or in conjunction with other retention members. For example, similarly formed and uniformly spaced retention members 42 may be located at positions around the chamber surface 41 to increase the gripping performance thereof during use. For example, as best shown in FIG. 4, a particular useful orientation of a plurality of retention members 42 would be to locate a plurality of retention members 42 in uniformly spaced apart locations around the circumference of the chamber 37. Such a grouping of retention members 42 are identified hereinafter as a "set" of retention members.

As shown in FIGS. 3–6, the set of retention members 42 includes three longitudinal ribs which are each positioned within the chamber 37 in uniformly spaced relationship around the circumference thereof. Each retention member 42 forms a tapered surface 44 at the proximal end thereof which tapers down to the chamber interior surface 41. The tapered surfaces 44 function to gradually compress the outer surface 49 of the sheath 29 as it is inserted into the cavity 31 of the shield 10.

As best shown in FIGS. 1–2 and 5–6, the shield 10 may also include circumferentially oriented retention members 50 located around the surface 41 of the channel 37 near the proximal opening 38, and a pair of elongate slots 51 oriented in the longitudinal direction of the shield 10 formed in the housing 36 extending from open end 38 toward the distal end of the sheath.

The slots 51 are oriented in radially opposed positions relative to each other and are formed of a sufficient width (b) that a user may squeeze the proximal end of the shield 10 to cause it to resiliently deform until the distal ends of slot surfaces 52 contact each other.

As is clearly evident, the result of squeezing the distal end of the shield 10 formed in accordance with this first embodiment of the present invention effectively reduces the diameter of the distal end opening 38 and causes the retention members 50 as best shown in FIG. 3, to be forced into surface 49 of the sheath 29 to increase the gripping power and frictional resistance between the shield 10 and the sheath 29. Thus, although retention members 42 can securely retain the sheath 29 within the shield 10 during normal use, the retention members 50 along with the slots 51 allow a significant increase in the retention abilities of the sheath 10 which can be useful for initial removal of a sheath 29 from the hub 13 in cases where excessive adhesion has developed between the hub surface 21 and the sheath 29, such as may be caused by material interactions therebetween during storage.

As shown in a second alternative embodiment of the shield 10, as shown in FIG. 7, it may however be advantageous to form the shield 10 without the slots 51 or retention members 50, specifically if there is no need to overcome an initial adhesion force between the hub 13 and sheath 29.

In a third alternative embodiment of the shield 10, as shown in FIG. 8, a proximal set of retention members 43 are located within chamber 37 in uniform spaced apart relationship as in the manner described above with respect to the second preferred embodiment of the invention, yet the retention member 43 do not extend along the entire length of the chamber 37 as do retention members 42. Instead, a second set of retention members 45 are located with the chamber 37 and are rotated relative to the retention members 43 such that each retention member 45 is located between a retention member 43, and retention members 45 extend generally the remainder of the length of the chamber 37. Retention members 43 and 45 together can extend substantially the entire length of chamber if desired, 37 and function substantially in the same manner as retention members 42 described in conjunction with FIGS. 3-6 above. Also, if desired, the third alternative embodiment of the shield 10 may include the slots 51 and retention members 50 at the proximal end thereof, with retention members 43 and 45 being shortened somewhat and located centrally and proximally, respectively, in chamber 37.

It should be understood that although only two orientations of retention members 42 and/or retention members 43 and 45 have been shown in the accompanying drawings, it is to be understood that any number of retention members can be employed as a set, and any number of sets of retention members may be employed in conjunction with any desired relative orientation of retention members or sets thereof. The particular numbers, orientations, and locations of retention members shown in the drawings are merely exemplary of the general concept in this regard.

In either of the first or second preferred embodiment of the present invention it is clear that a shield 10 can be manufactured to a "generic" size, and subsequently used to retrofit a plurality of various sizes or lengths of sheath/needle cannula sub-assemblies of various prefilled hypodermic syringe assembly designs (which of course may be similar to, or very different from, the syringe assembly 11 shown in the drawings).

The shield 10 of the present invention as shown in FIGS. 1 through 9 can be manufactured in a plurality of ways. One of the preferred methods of manufacturing the present invention is to form the housing 36 with chamber 37 therein in a single manufacturing process such as injection molding, with the retention members 42 integrally formed therewith. As stated above, the housing 36 will include an open proximal end 38 formed as a part of channel 37, (opening 38 having generally the same diameter as the interior surface 41). The housing 36 may optionally include projections 40, closed end 39, stop elements 46 and reinforcement ribs 48, all formed integrally therewith as desired.

The molding process and the tool used therefor, can be chosen to form the appropriate size and protrusion of retention members 42 for proper functioning of the shield during insertion and retention of the sheath 29 therein. For example, as shown in FIG. 4, a shield 10 having a cylindrical chamber 37 with an interior diameter of approximately 0.21 inches, may be formed with a set of retention members 42 therein which effectively reduce the diameter (d) through which the sheath 29 must pass to approximately 0.16 inches. A sheath 29 having an outer diameter of approximately 0.19 inches would therefore be required to contact the tapered proximal surface 44 of the retention member 42 to force the sheath surface 49 to into compression while the sheath 29 moves therepast into a completely inserted position within chamber 37. In the instance as shown in FIG. 4, where three retention members 42 are utilized, this would necessitate each retention member 42 being formed of a radius (r) of approximately 0.03 inches.

As the sheath 29 is inserted into cavity 31, the retention members 42 compress surface 49 of the sheath 29. The compression force applied to sheath 29 and the frictional resistance force between sheath surface 49 and the retention members 42 tends to force sheath 29 against hub 13. These insertion forces are resisted by the shoulder 47 of hub 13.

The shield 10 of the present invention is very simple and reliable in use. For example, a medical worker can merely insert the sheath/needle cannula sub-assembly of a hypodermic syringe assembly 11 into the shield 10 at any time prior to its use. If desired, the hypodermic syringe assembly 11 may be manufactured as a unit and packaged singly or in quantities, separate apart from the shield 10. The shield 10 may be similarly packaged separately from the syringe 11, either singly or in quantities. A medical worker would then perform the retrofit procedure him or herself by removing an assembly 11 from its sterile package and a shield 10 from its package, and retrofitting the shield 10 thereto by inserting the sheath/needle cannula sub-assembly completely into chamber 37. In this manner, the sterility of the needle cannula 12 is unaffected by the retrofit procedure, and the assembly 11 is made substantially safe from inadvertent needle sticks which may have resulted from bumping or applying excessive pressure to the distal end 35 of the sheath 29 prior to the positioning of the shield 10 thereover.

When it is desired to use the syringe assembly 11 to deliver the medication 15 therein to a patient, the medical worker can remove shield 10 from the assembly 11, which simultaneously causes the removal of sheath 29 therewith, thus exposing the needle for use. Once the sheath 29 is removed from the needle cannula 12, a piston arm (not shown) can be attached to threaded end 28 of the piston 16 if desired, and the medical worker can then administer the medication 15 to the patient.

At times, particular interactions between the materials forming the hub 13 and the sheath 29 tend to cause adhesion. The sheath 29 and hub surface 21 may become "stuck" together so that an initial high pulling force may be required for their separation. Other factors, such as manufacturing specifications, storage time, temperature, the presence of excess medication in the prefilled process, etc., may also cause the sheath 29 to be difficult to separate from the hub 13. In such instances, it may be advantageous for the medical worker, prior to attempting removal of the shield 10 by pulling it away from the remainder of the syringe assembly 11 to first squeeze the proximal end of the shield 10 in order to increase the gripping power of the retention members and insure that the sheath 29 will be retained within the shield 10 when removed. This will cause any incidental bonding between the sheath 29 and the hub 13 to be overcome during withdrawal of the shield 10. If so, the medical worker may squeeze the proximal end of the housing 36 of the shield 10 to cause the distal end opening 38 to be reduced in diameter and to cause retention members 50 to be forces into the surface 49 of the sheath 29. The medical worker than removes the sheath 10 while maintaining the grip at the proximal end thereof until any excessive adhesion between the sheath 29 and the hub 13 is overcome.

After use, should it be necessary for the medical worker to reinsert the needle cannula 12 into the sheath 29, the medical worker is substantially protected from a needle stick of the type which results from the misalignment of the needle cannula 12 in the sheath 29 and which causes tip 19 thereof to prematurely penetrate the sheath plug material 30 and "skive" off from its intended path and protrude through the exterior surface 49. Should such occur, instead of the medical worker receiving a stick from the tip 19 of the needle cannula 12, the tip 19 will become embedded in the substantially impermeable housing 36 of the shield 10 and be prevented from reaching the medical workers hand.

It will be apparent from the forgoing, while particular embodiments have been illustrated and described, various modifications can be made thereto without departing from the spirit and scope of the invention. Accordingly, it is not intended that the invention be limited, except as by the appended claims.

What is claimed is:

1. A shield for a hypodermic syringe assembly which includes a sheath/needle sub-assembly having a resilient sheath covering a distal portion of a needle cannula, said shield comprising:

a relatively rigid housing forming an elongate chamber therein said chamber forming an open proximal end, and said chamber and said open proximal end having cross-sectional areas sized to allow the sheath/needle sub-assembly to be inserted through said open proximal end and into said chamber, said relatively rigid housing further forming a pair of slots extending longitudinally along said shield from said open proximal end thereof, said slots extending through said housing into said chamber, and said slots being located at opposite positions in said chamber; and retention means formed as a part of said housing for holding the sheath in said chamber and for preventing separation of the sheath from said shield when the needle cannula is removed from the sheath;

whereby said shield is easily positionable over the sheath/handle sub-assembly, and the sheath, when engaged within said shield, is easy removed from the needle cannula by exerting a gripping force on said housing near said open proximal end thereof to resiliently deform said housing to form an effective cross-sectional area of said chamber which is less than the cross-sectional area of the sheath, and withdrawing said shield from the needle cannula.

2. A shield according to claim 1 wherein said retention means includes at least one retention member projecting into said chamber and functioning to allow movement of the sheath/needle sub-assembly into said chamber and to subsequently inhibit movement of the sheath out of said chamber.

3. A shield according to claim 2 wherein said at least one retention member is an elongate rib extending longitudinally within said chamber.

4. A shield according to claim 2 wherein said at least one retention member includes a tapered proximal end surface which contacts and compresses the sheath during insertion thereof.

5. A shield according to claim 1 wherein said housing is formed of a generally cylindrical outer surface and said chamber is formed of a generally cylindrical inner surface.

6. A shield according to claim 5 wherein said housing includes a plurality of reinforcement ribs integrally formed with an extending longitudinally along said cylindrical outer surface of said housing.

7. A shield according to claim 3 including a plurality of said retention members, said plurality of retention members forming at least one set of retention members spaced uniformly about a circumference of said chamber.

8. A shield according to claim 7 including at least two of said sets of retention members, each of said sets being located at a different longitudinal position along said chamber.

9. A shield according to claim 8 wherein each of said sets are located at different longitudinal and circumferential positions around said chamber.

10. A shield according to claim 1 wherein said cross-sectional area of said chamber is a circular area and said effective cross-sectional area is an effective circular area formed by said retention means.

11. A shield according to claim 10 wherein said circular area is approximately 0.21 inches in diameter and said effective circular area is approximately 0.16 inches in diameter.

12. A shield according to claim 1 wherein said retention means includes at least one elongate rib of semi-circular cross-section.

13. A shield according to claim 12 wherein said semi-circular cross-section of said rib has a radius of approximately 0.03 inches.

14. A shield according to claim 1 further including stop means located adjacent said distal end of said chamber, for abutment against a distal end of the sheath to prevent insertion of the sheath beyond said stop means.

15. A shield according to claim 14 wherein said stop means includes a closed distal end.

16. A shield according to claim 1 further including flange means integrally formed with and extending radially outward from said housing at a location adjacent said open proximal end of said chamber.

17. A shield according to claim 1 made from polypropylene.

18. A shield according to claim 1 made from polyethylene.

19. A shield according to claim 14 wherein said chamber includes an open distal end.

20. A method of using a shield for a hypodermic syringe assembly which includes a sheath/needle sub-assembly having a resilient sheath covering the distal portion of a needle cannula, the sheath including a relatively rigid housing forming an elongate chamber therein, the chamber having an open proximal end and a retention means including at least one retention member located within the elongate chamber away from the chamber open end and formed as a part of the housing, for holding the sheath within the chamber and for preventing separation of the sheath from the chamber when the needle cannula is removed, the relatively rigid housing further including a pair of slots extending longitudinally along the shield from the open proximal end thereof, the slots extending through the housing into the chamber, and the slots being located at opposing positions in the chamber, said method of using the shield comprising the steps of:

inserting the sheath/needle sub-assembly through the open proximal end of the chamber until the sheath engages with the retention means;

removing the sheath from the needle cannula by exerting a gripping force on the housing near the open proximal end thereof to resiliently deform the housing to form an effective cross-sectional area of the chamber which is less than the cross-sectional area of the sheath and removing the shield from the needle cannula while the retention means holds the sheath in place therein.

21. A method according to claim 20 further including the step of:
replacing the sheath with the shield affixed thereabout, over the needle cannula.

22. A method according to claim 21 further including the step of:
removing the hypodermic syringe assembly from a sterile package prior to inserting the sheath/needle sub-assembly thereof into the shield.

23. A method according to claim 20 wherein the retention means includes at least one retention member projecting into the chamber and said step of inserting the needle/sheath sub-assembly until the sheath engages with the retention means includes engaging the sheath with the at least one retention member, the retention member functioning to allow movement of the sheath/needle sub-assembly into the chamber, and said step of removing the sheath from the needle cannula includes at least one retention member functioning to inhibit movement of the sheath out of the chamber.

24. A method according to claim 23 wherein the shield includes a plurality of retention members forming at least two sets of retention members, each set of retention members including a plurality of retention members space uniformly about a circumference of the chamber and each set of retention members being located at a different longitudinal position around the chamber, said step of inserting the sheath/needle sub-assembly into the chamber further includes engaging at least one of the sets of retention members with the sheath.

25. A method according to claim 24 wherein said step of engaging the sheath with the retention members includes engaging said sheath with only one set of retention members.

26. A method according to claim 24 wherein said step of engaging the sheath with the retention members includes engaging the sheath with at least two sets of retention members.

27. A method according to claim 20 wherein the chamber is cylindrical in shape having a circular cross-sectional area through which the sheath must pass during insertion, and the retention means forms an effective cross-sectional area which is less than the cross-sectional area of the chamber and less than the cross-sectional area of the sheath, said step of inserting the sheath/needle sub-assembly into the chamber further including the step of resiliently compressing the sheath by the retention means prior to removal thereof from the needle cannula.

28. A method according to claim 20 wherein the shield further including stop means located adjacent the distal end of the chamber and said method further includes the step of abutting a distal end of the sheath against the stop means at the completion of said inserting step, the stop means functioning to prevent further insertion of the sheath into the chamber beyond the stop means.

29. A shield for a hypodermic syringe assembly which includes a sheath/needle sub-assembly having a resilient sheath covering a distal portion of a needle cannula, said shield comprising:
a relatively rigid housing forming an elongate chamber therein, said chamber forming an open proximal end, and said chamber and said open proximal end having cross-sectional areas sized to allow the sheath/needle sub-assembly to be inserted through said open proximal end and into said chamber, said relatively rigid housing further forming a pair of slots extending longitudinally along said shield from said open proximal end thereof, said slots extending through said housing into said chamber, and said slots being located at opposing positions in said chamber; and
retention means formed as a part of said housing for holding the sheath in said chamber and for preventing separation of the sheath from said shield when the needle cannula is removed from the sheath;
whereby said shield is easily positionable over the sheath/needle sub-assembly, and the sheath, when engaged within said shield, is easily removed from the needle cannula by exerting a gripping force on said housing near said open proximal end thereof to resiliently deform said housing to form an effective cross-sectional area of said chamber which is less than the cross-sectional area of the sheath, and withdrawing said shield from the needle cannula.

30. A shield according to claim 29 wherein said retention means includes at least one circumferential retention member projecting into said chamber and functioning to allow movement of the sheath/needle sub-assembly into said chamber and to subsequently inhibit movement of the sheath out of said chamber.

31. A shield according to claim 30 wherein said at least one retention member is an elongate rib extending longitudinally within said chamber.

32. A shield according to claim 30 wherein said at least one circumferential member is an elongate rib extending circumferentially around a portion of said chamber.

33. A shield according to claim 32 wherein said at least one circumferential retention member is located between said pair of slots.

34. A shield according to claim 30 wherein said at least one longitudinal retention member includes a tapered proximal end surface which contacts and compresses the sheath during insertion thereof.

35. A shield according to claim 29 wherein said housing is formed of a generally cylindrical outer surface and said chamber is formed of a generally cylindrical inner surface.

36. A shield according to claim 35 wherein said housing includes a plurality of reinforcement ribs integrally formed with an extending longitudinally along said cylindrical outer surface of said housing.

37. A shield according to claim 30 including a plurality of said retention members, said plurality of retention members forming at least one set of retention members spaced uniformly about a circumference of said chamber.

38. A shield according to claim 37 including at least two of said sets of retention members, each of said sets being located at a different longitudinal position along said chamber.

39. A shield according to claim 29 wherein said cross-sectional area of said chamber is a circular area and said effective cross-sectional area is an effective circular area formed by said retention means.

40. A shield according to claim 29 further including stop means located adjacent said distal end of said chamber, for abutment against a distal end of the sheath to prevent insertion of the sheath beyond said stop means.

41. A shield according to claim 40 wherein said stop means includes a closed distal end.

42. A shield according to claim 29 further including flange means integrally formed with and extending radially outward from said housing at a location adjacent said open proximal end of said chamber.

43. A shield according to claim 29 made from polypropylene.

44. A shield according to claim 29 made from polyethylene.

45. A shield according to claim 40 wherein said chamber includes an open distal end.

* * * * *